(12) United States Patent
Maruta

(10) Patent No.: US 10,863,114 B2
(45) Date of Patent: Dec. 8, 2020

(54) RADIATION IMAGE CAPTURING APPARATUS

(71) Applicant: Konica Minolta, Inc., Chiyoda-ku, Tokyo (JP)

(72) Inventor: Yuuichi Maruta, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 298 days.

(21) Appl. No.: 15/662,710

(22) Filed: Jul. 28, 2017

(65) Prior Publication Data

US 2018/0035060 A1   Feb. 1, 2018

(30) Foreign Application Priority Data

Jul. 29, 2016 (JP) ................. 2016-149144
Jul. 20, 2017 (JP) ................. 2017-140488

(51) Int. Cl.
| | | |
|---|---|---|
| *H04N 5/32* | (2006.01) | |
| *H04N 5/335* | (2011.01) | |
| *H04N 5/343* | (2011.01) | |
| *H04N 5/349* | (2011.01) | |
| *H04N 5/353* | (2011.01) | |
| *H04N 5/369* | (2011.01) | |
| *H04N 5/374* | (2011.01) | |
| *H04N 5/376* | (2011.01) | |
| *A61B 6/00* | (2006.01) | |
| *H04N 5/345* | (2011.01) | |

(52) U.S. Cl.
CPC ................ *H04N 5/32* (2013.01); *A61B 6/50* (2013.01); *H04N 5/335* (2013.01); *H04N 5/343* (2013.01); *H04N 5/349* (2013.01); *H04N 5/3454* (2013.01); *H04N 5/353* (2013.01); *H04N 5/369* (2013.01); *H04N 5/374* (2013.01); *H04N 5/376* (2013.01)

(58) Field of Classification Search
CPC ............ H04N 5/32; H04N 5/335; A61B 6/50
See application file for complete search history.

(56) References Cited

U.S. PATENT DOCUMENTS

2013/0341525 A1* 12/2013 Maruta ..................... G01T 1/17
                                                                       250/394

FOREIGN PATENT DOCUMENTS

| JP | 3897389 | B2 | 3/2007 |
|---|---|---|---|
| JP | 2008042478 | A | 2/2008 |
| JP | 5627748 | B2 | 11/2014 |
| JP | 5749873 | B1 | 7/2015 |

\* cited by examiner

*Primary Examiner* — Hugh Maupin
(74) *Attorney, Agent, or Firm* — Cantor Colburn LLP

(57) ABSTRACT

A radiation image capturing apparatus includes scan lines of $1^{st}$ to $n^{th}$ lines, scan driving units, a controller, an OE signal line and a CPV signal line. The OE signal line is to input OE signal by which an ON voltage is applied to a scan line. The CPV signal line is to input CPV signal by which the scan line, to which the ON voltage is applied by the input of the OE signal, is shifted to a next scan line. To the scan driving units, the controller inputs the CPV signal to sequentially shift the scan line from the $1^{st}$ line to the $n^{th}$ line, and inputs the OE signal to apply the ON voltage only when the scan line is a scan line of an effective pixel region from which image data is read.

10 Claims, 8 Drawing Sheets

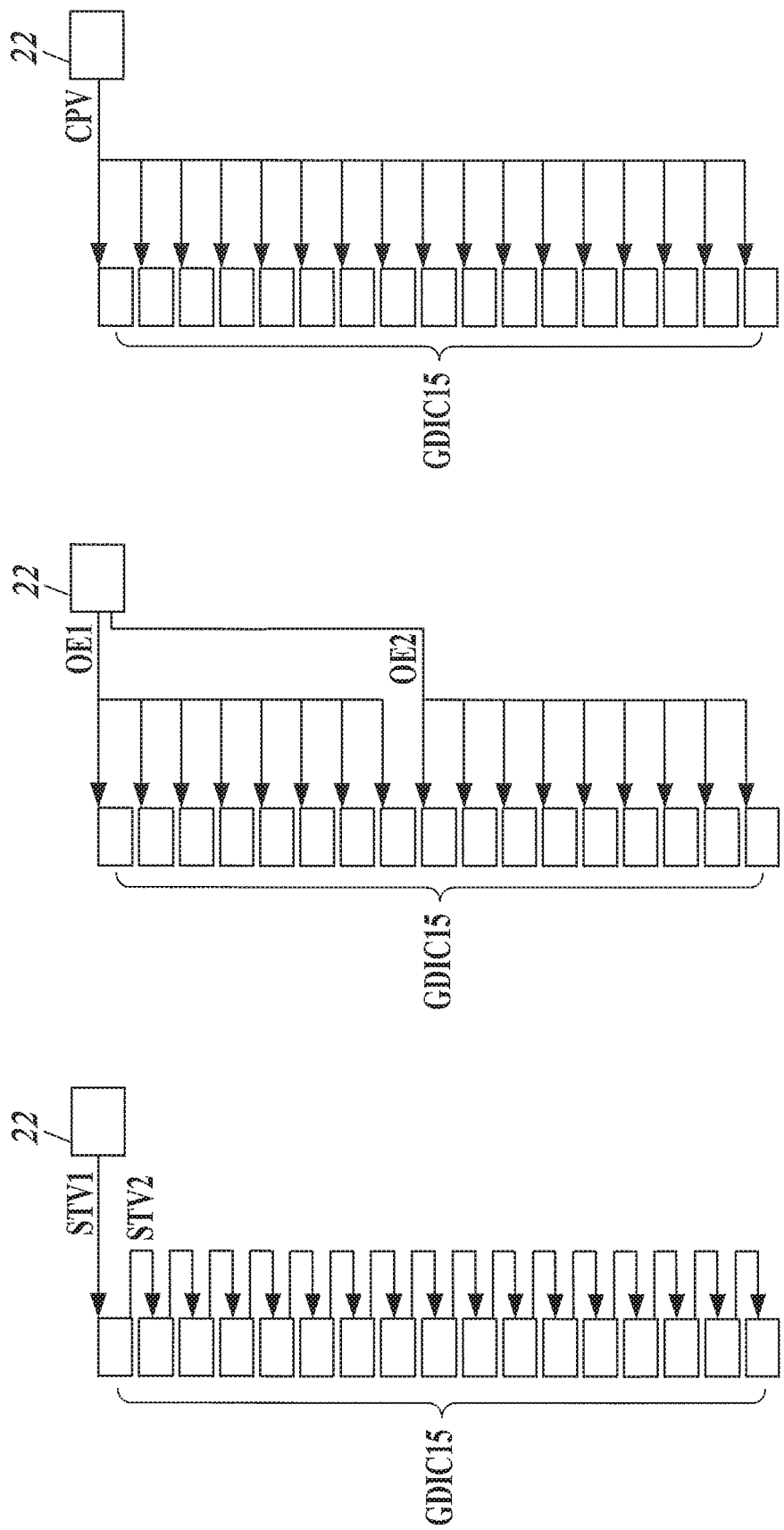

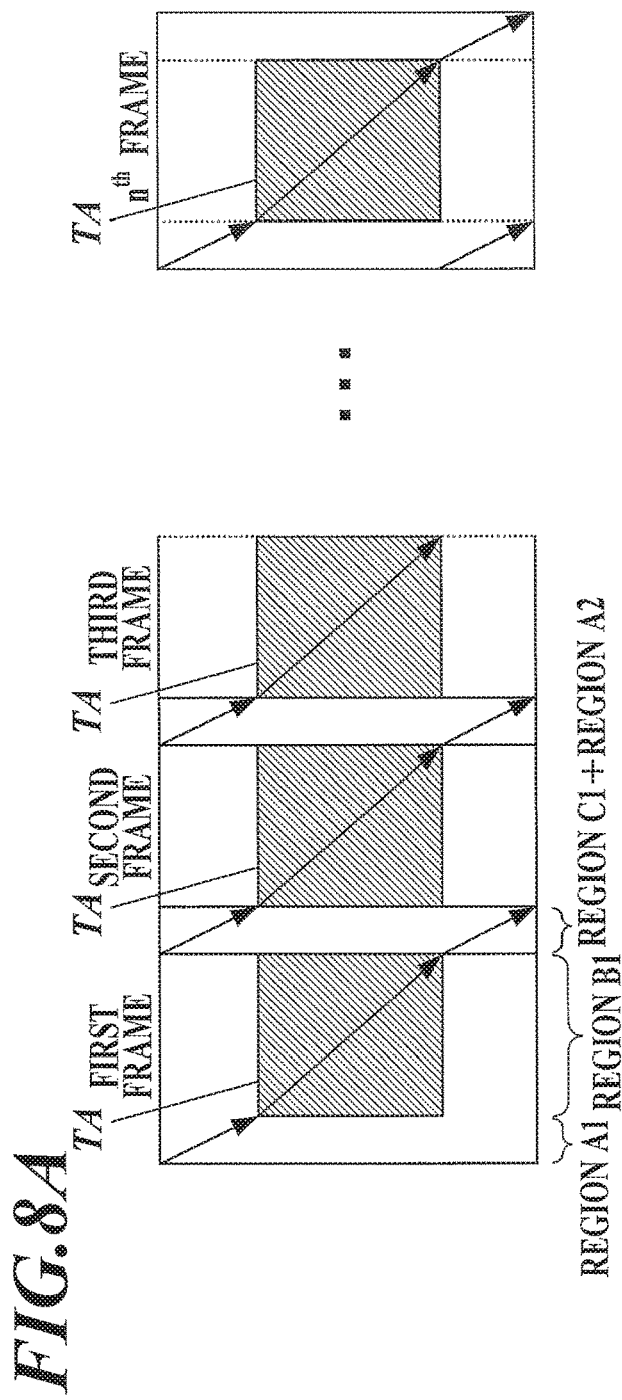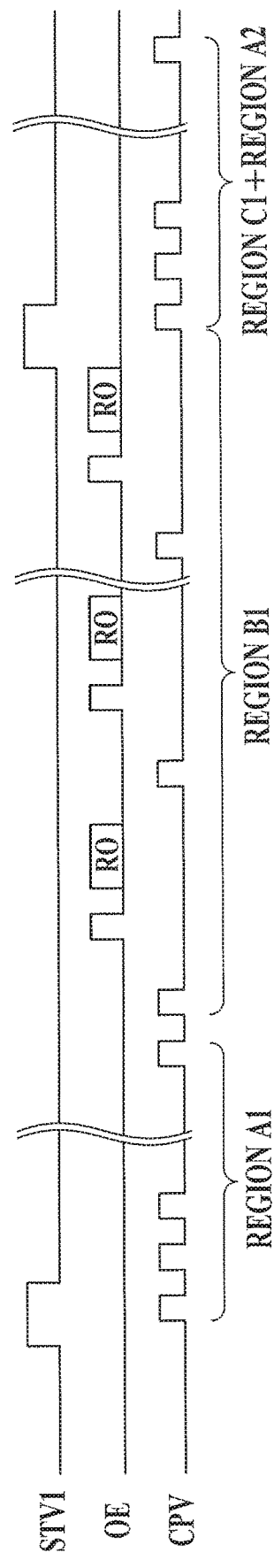
FIG. 8A
FIG. 8B

RADIATION IMAGE CAPTURING APPARATUS

CROSS-REFERENCE TO RELATED APPLICATIONS

The present invention claims priority under 35 U.S.C. § 119 to Japanese Patent Application No. 2016-149144, filed on Jul. 29, 2016, and Japanese Patent Application No. 2017-140488, filed on Jul. 20, 2017, the entire contents of which are incorporated herein by reference.

BACKGROUND

Technological Field

The present invention relates to a radiation image capturing apparatus.

Description of the Related Art

There have been developed a variety of radiation image capturing apparatuses (Flat Panel Detectors) in each of which radiation detectors are two-dimensionally arranged and electric charges generated in the radiation detectors according to the dose(s) of radiation that has been emitted from a radiation emission apparatus and passed through a subject are read as image data. These radiation image capturing apparatuses are used for image capturing (hereinafter may simply be called "imaging") at facilities, such as hospitals. Recently, portable radiation image capturing apparatuses have been developed and come into practical use. The portable radiation image capturing apparatuses are each formed by placing, in a housing, a sensor panel or the like on which radiation detectors and other components are formed.

These radiation image capturing apparatuses can perform still image capturing (also called plain radiography, general radiography, etc.), thereby capturing one radiation image each time irradiated with radiation via a subject, as with conventional silver halide films, CR (Computed Radiography) cassettes having built-in stimulable phosphor sheets, and so forth.

In the case of the conventional silver halide films and CR cassettes, if they are continuously irradiated with radiation via a subject, a problem of, for example, double exposure or multiple exposure arises. Meanwhile, the radiation image capturing apparatuses can each transfer data (i.e. image data) of captured radiation images to external apparatuses or store the data in a memory built therein.

Hence, unlike the conventional silver halide films and CR cassettes, the radiation image capturing apparatuses can also perform moving image capturing, thereby continuously obtaining radiation images, in order to observe the dynamic state of the lungs of a patient who has a lung problem, such as ventilation or perfusion (blood flow) of the lungs, and quasi moving image capturing, such as tomosynthesis imaging, thereby capturing radiation images of multiple frames in such a way as to be continuous in terms of time like a moving image by being, for example, continuously irradiated with radiation via a subject. The tomosynthesis imaging is capturing radiation images of a subject while moving a radiation image capturing apparatus and a radiation emission apparatus.

However, when a radiation image capturing apparatus continuously captures radiation images of multiple frames as described above, radiation emission and a signal readout process to read signals need to be repeated multiple times in a sequence of imaging. The longer the time required for the signal readout process is, the longer the time required for imaging is, which puts a great strain on patients.

The radiation image capturing apparatus can capture images not only by using the entire region in which imaging is available (hereinafter called "imaging available region"), but also by using only an area (hereinafter called "irradiation area") in the imaging available region, the area corresponding to a site/part that is a diagnosis target and irradiated with radiation. Then, in Japanese Patent Nos. 3897389, 5749873 and 5627748 and Japanese Patent Application Publication No. 2008-42478, it is proposed, when imaging is performed with the irradiation area limited, to perform trimming control by which the signal readout process is performed only on an effective pixel region (region of interest) irradiated with radiation so as to reduce the time required for the signal readout process.

Performing the signal readout process only on the effective pixel region (region of interest) can increase the frame rate.

In order to read signals of image data captured by a radiation image capturing apparatus, it is necessary to control the signal readout process by appropriately inputting various signals from a controller to devices (scan driving units) that perform gate driving. In the conventional art, signal lines to input these various signals are connected from the controller to the scan driving units individually.

When the signal lines are connected from the controller to the scan driving units individually, the signals can be input to any scan driving unit(s) that belongs any region(s) flexibly, and hence it is easy to perform the signal readout process only on the effective pixel region (region of interest).

When the signal lines are connected from the controller to the scan driving units individually, however, the required number of I/O ports of the controller, such as an FPGA, which controls the scan driving units is large, and in order to ensure the required number of I/O ports, it may be necessary to use an upper class package.

Further, because many lines need to be drawn from the circuit (i.e. the controller, e.g. an FPGA), which controls the scan driving units, the configuration of a board becomes intricate, and also, in order to ensure paths for the drawn lines, the board needs to have a large number of layers, so that cost increase is unavoidable.

In particular, these days, resolution of the radiation image capturing apparatuses (Flat Panel Detectors) has been increased, and accordingly the number of the scan driving units provided in the radiation image capturing apparatuses has been increased.

Thus, cost increase due to increase in the required number of I/O ports of the controller, which controls the scan driving units, intricate wiring, increase in the required number of layers of the board to ensure the paths for the drawn lines, and so forth has become an extremely important problem, and trimming control that focuses only on increase in the frame rate has limits.

SUMMARY

The present invention has been conceived in view of the above problems, and objects of the present invention include providing a radiation image capturing apparatus by which the required number of I/O ports of a controller that controls scan driving units can be reduced, and also the time required for the signal readout process (an image data D signal readout process described below) can be reduced by performing appropriate trimming control.

To achieve at least one of the abovementioned objects, according to an aspect of the present invention, a radiation image capturing apparatus reflecting one aspect of the present invention comprises: a plurality of scan lines of a $1^{st}$ line to an $n^{th}$ line; a plurality of signal lines; a plurality of radiation detectors two-dimensionally arranged in an imaging available region; a plurality of readout circuits that read electric charges released from the radiation detectors to the signal lines as image data; a plurality of switches that are arranged for the respective radiation detectors, and go into OFF state and break electrical continuity of the radiation detectors and the signal lines when OFF voltage is applied via the scan lines, and go into ON state and release the electric charges from the radiation detectors to the signal lines when ON voltage is applied via the scan lines; a plurality of scan driving units that switch voltage to be applied to the scan lines between the ON voltage and the OFF voltage; a controller that performs control to perform a readout process to read the image data from the radiation detectors; an OE signal line to input, from the controller to the scan driving units, OE signal by which the ON voltage is applied to a predetermined scan line and the switches on the predetermined scan line go into the ON state; and a CPV signal line to input, from the controller to the scan driving units, CPV signal by which the predetermined scan line, to which the ON voltage is applied by the input of the OE signal, is shifted to a next scan line, wherein the controller inputs the CPV signal to the scan driving units so as to sequentially shift the predetermined scan line from the $1^{st}$ line to the $n^{th}$ line, and inputs the OE signal to the scan driving units so as to apply the ON voltage only when the predetermined scan line is a scan line of an effective pixel region from which the image data is read.

BRIEF DESCRIPTION OF THE DRAWINGS

The advantages and features provided by one or more embodiments of the invention will become more fully understood from the detailed description hereinbelow and the appended drawings which are given by way of illustration only, and thus are not intended as a definition of the limits of the present invention, wherein:

FIG. 4A shows an example of wiring of STV signal lines in a first embodiment;

FIG. 4B shows an example of wiring of OE signal lines in the first embodiment;

FIG. 4C shows an example of wiring of a CPV signal line in the first embodiment;

FIG. 8A is an illustration schematically showing trimming control in a modification of the second embodiment; and FIG. 8B is a timing chart showing input timings of the STV signal, the OE signal and the CPV signal in the modification of the second embodiment.

DETAILED DESCRIPTION OF EMBODIMENTS

Hereinafter, one or more embodiments of the present invention will be described with reference to the drawings, However, the scope of the invention is not limited to the disclosed embodiments.

First Embodiment

A first embodiment of a radiation image capturing apparatus of the present invention is described with reference to FIG. 1 to FIG. 5B. The scope of the present invention is not limited to the illustrated embodiments.

Hereinafter, as the radiation image capturing apparatus, there is described, what is called, an indirect-type radiation image capturing apparatus that includes a scintillator, and with the scintillator, converts received radiation into light of another wavelength, such as visible light, and obtains image data with radiation detectors. However, the present invention is also applicable to, what is called, a direct-type radiation image capturing apparatus that directly detects received radiation with radiation detectors, not via a scintillator.

<Basic Configuration of Radiation Image Capturing Apparatus>

Figure 1:
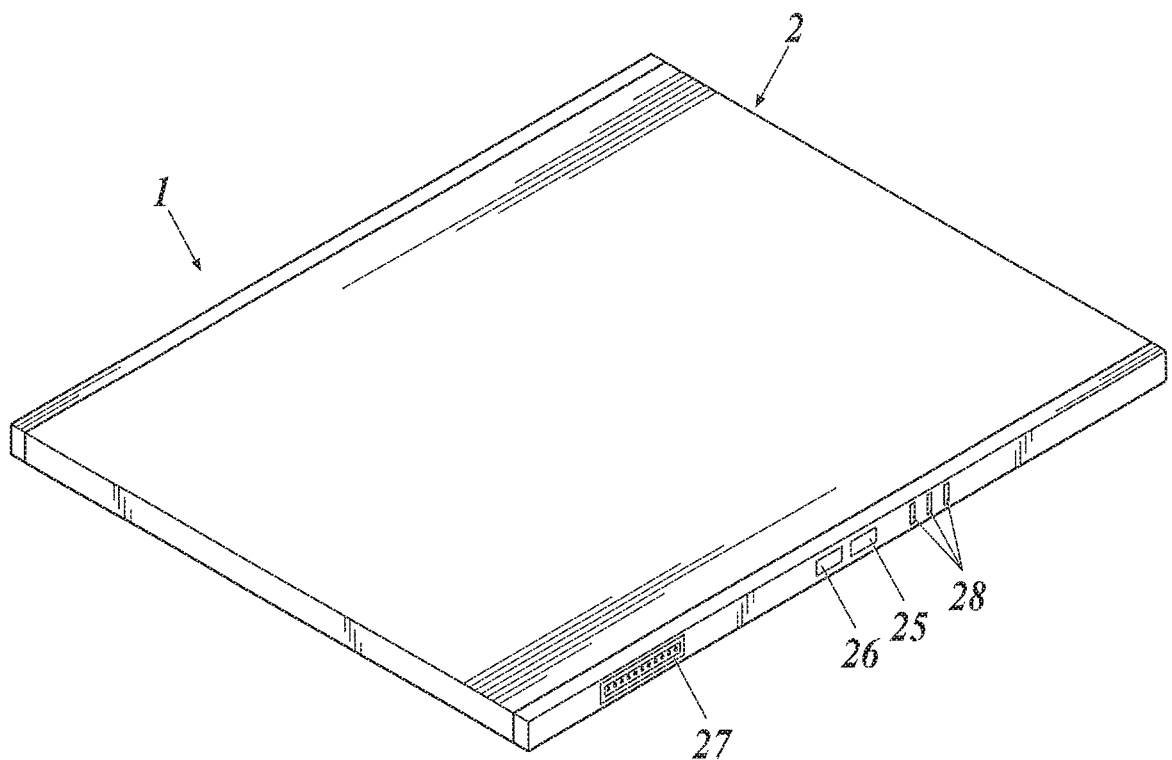
FIG. 1 is a perspective view showing the external appearance of a radiation image capturing apparatus according to embodiments of the present invention.

The basic configuration and so forth of the radiation image capturing apparatus of this embodiment are described. FIG. 1 is a perspective view showing the external appearance of a radiation image capturing apparatus of embodiments.

In this embodiment, a radiation image capturing apparatus 1 is formed by placing the below-described radiation detectors 7 and other components in a housing 2. One lateral surface of the housing 2 is provided with a power switch 25, a switch 26, a connector 27, indicators 28 formed of LEDs or the like, and so forth. Further, although not shown, in this embodiment, the opposite lateral surface or the like of the housing 2 is provided with an antenna 29 (see FIG. 2) for wireless communications with external apparatuses. The radiation image capturing apparatus 1 uses the antenna 29 for wireless communications with external apparatuses, and uses the connector 27 for wired communications with external apparatuses by a not-shown cable or the like being connected to the connector 27.

Figure 2:
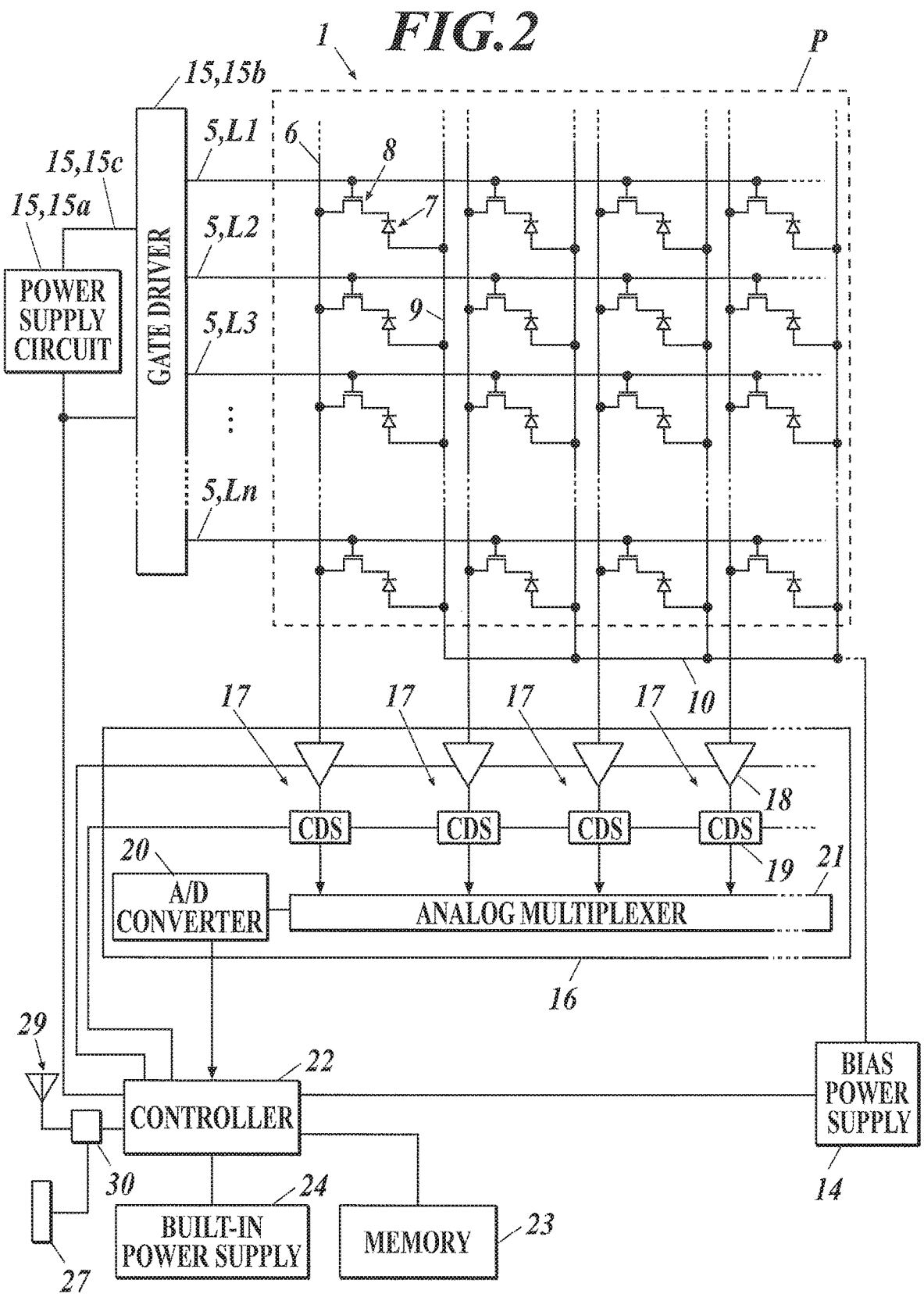
FIG. 2 is a block diagram showing an equivalent circuit of the radiation image capturing apparatus.

FIG. 2 is a block diagram showing an equivalent circuit of a radiation image capturing apparatus of embodiments. As shown in FIG. 2, in the radiation image capturing apparatus 1, the radiation detectors 7 are two-dimensionally (in a matrix) arranged in the imaging available region ("P" in FIG. 2) on a not-shown sensor board. The radiation detectors 7 generate electric charges according to the dose(s) of received radiation. The radiation detectors 7 are connected to bias lines 9, the bias lines 9 are connected to a tie line 10, and the tie line 10 is connected to a bias power supply 14, so that reverse bias voltage is applied from the bias power supply 14 to the radiation detectors 7 via the bias lines 9 and so forth.

The radiation detectors 7 are connected with thin film transistors (hereinafter "TFTs") 8 that are switches, and the TFTs 8 are connected to signal lines 6.

In scan driving units 15 that are gate driver ICs (GDICs), ON voltage and OFF voltage are supplied from a power supply circuit(s) 15a to gate drivers 15b via a line(s) 15c. The gate drivers 15b switch voltage to be applied to lines L1 to Ln of scan lines 5 between ON voltage and OFF voltage. The scan driving units 15, which are the gate driver ICs (GDICs) 15, are controlled by an FPGA (Field Programmable Gate Array) or the like.

When ON voltage is applied to the TFTs 8 via the scan lines 5, the TFTs 8 go into the ON state and release the electric charges accumulated in the radiation detectors 7 to the signal lines 6. On the other hand, when OFF voltage is applied to the TFTs 8 via the scan lines 5, the TFTs 8 go into the OFF state and break electrical continuity of the radiation detectors 7 and the signal lines 6 so that the electric charges generated in the radiation detectors 7 are accumulated therein.

In each readout IC 16, readout circuits 17 are provided. The readout circuits 17 are connected to the signal lines 6. In the image data D signal readout process to read signals of image data D, the electric charges are released from the radiation detectors 7 and flow into the readout circuits 17 via the signal lines 6, and voltage values equivalent to the amounts of the electric charges are output from amplifier circuits 18 of the readout circuits 17. Then, correlated sampling circuits ("CDS" in FIG. 2) 19 of the readout circuits 17 read the voltage values output from the amplifier circuits 18 as analog value image data D and output the same to the downstream side. The output image data D are sequentially sent to an A/D converter 20 via an analog multiplexer 21. The A/D converter 20 sequentially converts the received image data D into digital value image data D and outputs the same to a memory 23 so that the image data D are sequentially stored therein.

Figure 3:
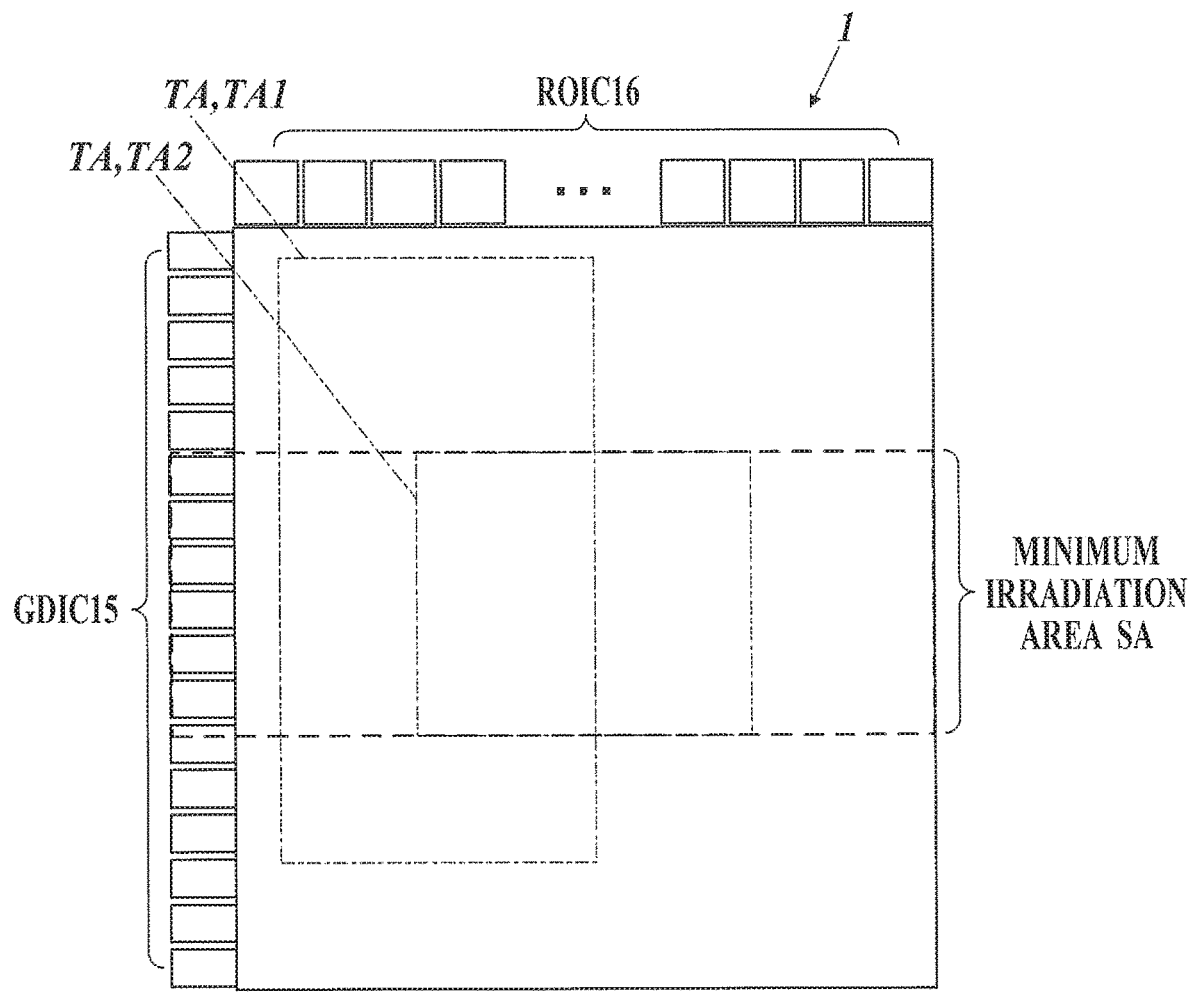
FIG. 3 is a schematic plan view of the radiation image capturing apparatus.

FIG. 3 is a schematic plan view of the radiation image capturing apparatus 1 of this embodiment.

As shown in FIG. 3, in this embodiment, 17 scan driving units 15, which are the gate driver ICs (each denoted by "GDIC 15" in FIG. 3), are arranged in the vertical direction of the radiation image capturing apparatus 1 (the direction vertical in FIG. 3).

In addition, 14 readout ICs 16 (each denoted by "ROIC 16" in FIG. 3) are arranged in the horizontal direction of the radiation image capturing apparatus 1 (the direction horizontal in FIG. 3).

The abovementioned numbers and arrangements of the scan driving units 15 and the readout ICs 16 are not limits but examples.

In this embodiment, trimming control is performed. In trimming control, an area from which signals of image data D is/are read is limited. Here, the "trimming control" is partial readout control to read signals of image data D only from (i.e. to perform the image data D signal readout process only on) the irradiation area (hereinafter "effective pixel region" or "region of interest"), which is irradiated with radiation, in the imaging available region where the radiation detectors 7 are arranged. Reading signals only from the effective pixel region can increase the frame rate.

For example, FIG. 3 shows two regions, an effective pixel region TA1 and an effective pixel region TA2 (regions indicated by dot-and-dash lines), which can be set as the effective pixel region (region of interest) TA from which image data D are read.

Of the effective pixel regions (TA1 and TA2 in FIG. 3) settable in the radiation image capturing apparatus 1, the vertical-direction range of the region (effective pixel region TA2 in FIG. 3) having the smallest vertical-direction range is taken as the minimum irradiation area SA (indicated by a broken line in FIG. 3) in the vertical direction to be irradiated with radiation. The area to be irradiated with radiation (i.e. the irradiation area) in imaging can be expanded in the up-down direction as far as it contains the minimum irradiation area SA.

Where to set the effective pixel region TA can be determined arbitrarily according to specifications, uses and so forth of the radiation image capturing apparatus 1, and hence is not limited to the illustrated examples.

Further, how to set the effective pixel region TA is not particularly limited.

For example, for each radiation image capturing apparatus 1, the effective pixel region (region of interest) TA, which is used in trimming control, may be preset. In this case, an indication indicating the region may be attached to the surface of each radiation image capturing apparatus 1 so that an operator (user), such as a radiologist, can visually confirm its effective pixel region TA. The technique for attaching the indication indicating the effective pixel region TA is not particularly limited. Examples thereof include printing, such as screen printing.

Alternatively, the effective pixel region TA may be set from an external operation apparatus, such as a console (not shown). In this case, an operator (user) may be able to set an arbitrary area as the effective pixel region TA or may be able to select the effective pixel region TA from among one or more settable effective pixel regions that are different in size, location and/or the like, so that the effective pixel region TA in imaging is set.

Still alternatively, an operator may set the irradiation area of the radiation image capturing apparatus 1 according to the area/size or the like of a site desired to be imaged (hereinafter "imaging target site"), and the actual irradiation area actually irradiated by exposure to radiation may be set as the effective pixel region TA so that image data D are read from this region only. In this case, the radiation image capturing apparatus 1 may be provided with a not-shown X-ray sensor(s) so that the controller 22 can detect the (actual) irradiation area based on an output value(s) of the X-ray sensor(s). Alternatively, with no X-ray sensor, the controller 22 may detect the (actual) irradiation area based on output values of the radiation detectors 7 that are used in imaging, and set this area as the effective pixel region TA.

The controller 22 is constituted of, for example, a computer or an FPGA (Field Programmable Gate Array). The computer includes a CPU (Central Processing Unit), a ROM (Read Only Memory), a RAM (Random Access Memory) and an input-output interface that are connected to a bus (all not shown). The controller 22 may be constituted of a specialized control circuit. The controller 22 is connected with the memory 23 constituted of, for example, an SRAM (Static RAM), an SDRAM (Synchronous DRAM) or an NAND flash memory, and also connected with a communication unit 30 for wireless or wired communications with external apparatuses via the antenna 29 or connector 27.

The controller 22 is also connected with, for example, a built-in power supply 24 that supplies power necessary for components such as the scan driving units 15, the readout circuits 17, the memory 23 and the bias power supply 14. In the image data D signal readout process, the controller 22 controls actions of the scan driving units 15, the readout circuits 17 and so forth such that the readout circuits 17 and so forth read, as image data D, the electric charges released from the radiation detectors 7 to the signal lines 6 as described above.

In this embodiment, the radiation image capturing apparatus 1 can perform moving image capturing, thereby continuously obtaining radiation images, in order to observe the dynamic state of the lungs of a patient, such as ventilation or perfusion (blood flow) of the lungs, and quasi moving image capturing, such as tomosynthesis imaging, thereby capturing radiation images of multiple frames in such a way as to be continuous in terms of time like a moving image by being, for example, continuously irradiated with radiation via a subject. The tomosynthesis imaging is capturing radiation images of a subject while moving the radiation image capturing apparatus 1 and a not-shown radiation emission apparatus.

The controller 22 performs imaging in cooperation with a not-shown radiation emission apparatus according to imaging conditions (e.g. continuous imaging for dynamic state observation, tomosynthesis imaging or other types of imaging; pulsed radiation emission or continuous radiation emission; radiation emission time or the number of times radiation is emitted; time interval from one radiation emission to the next radiation emission; etc.) under which imaging is performed, and performs the image data D signal readout process.

Before imaging, the controller 22 causes the gate drivers 15b (see FIG. 2) of the scan driving units 15 to sequentially apply ON voltage to the lines L1 to Ln of the scan lines 5 so as to release the remaining electric charges in the radiation detectors 7 to the signal lines 6, thereby resetting the radiation detectors 7 (hereinafter "radiation detector 7 reset process").

When an operator, such as a radiologist, operates an exposure switch of the not-shown radiation emission apparatus, an emission start signal is sent from the radiation emission apparatus to the radiation image capturing apparatus 1. When receiving it, the controller 22 of the radiation image capturing apparatus 1 finishes the radiation detector 7 reset process, which is being performed at the time, after the gate driver 15b for the last line Ln of the scan lines 5 apples ON voltage to the last line Ln, and then causes the gate drivers 15b to apply OFF voltage to the lines L1 to Ln of the scan lines 5 so as to shift to an electric charge accumulation state, in which electric charges are accumulated. At the time, the controller 22 sends an interlock release signal to the radiation emission apparatus.

When receiving the interlock release signal from the radiation image capturing apparatus 1, the radiation emission apparatus emits radiation. The controller 22 of the radiation image capturing apparatus 1 causes the gate drivers 15b to sequentially apply ON voltage to the lines L1 to Ln of the scan lines 5 when a predetermined time elapses from the start of the electric charge accumulation state so as to perform the image data D signal readout process.

The read image data D may be transferred to a not-shown external image processer or the like every imaging (i.e. every frame), or may be stored in the memory 23 (see FIG. 2) of the radiation image capturing apparatus 1 and later transferred all together to the image processer or the like.

The radiation image capturing apparatus 1 of this embodiment can be used for imaging by being fitted into a not-shown imaging table, or can be used solo without being fitted into the imaging table, for example, by being placed on a patient, who is a subject, or by being inserted between a patient and a not-shown bed.

<Wiring on Board of Radiation Image Capturing Apparatus>

Next, wiring on the board of the radiation image capturing apparatus 1 of this embodiment is described in detail.

FIG. 4A is an illustration to explain wiring of STV (STart Vertical) signal lines for start-in-vertical-direction signal (hereinafter "STV signal") from the controller 22, FIG. 4B is an illustration to explain wiring of OE (Output Enable) signal lines for OE signal from the controller 22, and FIG. 4C is an illustration to explain wiring of a CPV (Clock Pulse Vertical) signal line for CPV signal from the controller 22.

As shown in FIG. 4A, in this embodiment, the STV signal line for gate input signal (hereinafter "STV1") of the STV signal is connected from the controller 22 only to the top scan driving unit (GDIC) 15, and the STV signal line for gate output signal (hereinafter "STV2") of the STV signal is connected from the top scan driving unit (GDIC) 15 to the next (i.e. the second from the top) scan driving unit (GDIC) 15 in a daisy chain.

In this embodiment, the imaging available region of the radiation image capturing apparatus 1 is divided into two divisional regions on the upper side and the lower side. As shown in FIG. 4B, of the OE signal lines to and through which the OE signal (OE1, OE2) is input from the controller 22, the OE signal line for OE1 is connected from the controller 22 to (i.e. is common to) the scan driving units (GDICs) 15 that belong to the divisional region on the upper side (hereinafter "upper region"), and the OE signal line for OE2 is connected from the controller 22 to (i.e. is common to) the scan driving units (GDICs) 15 that belong to the divisional region on the lower side (hereinafter "lower region").

Where to divide the imaging available region into the upper region and the lower region can be determined arbitrarily, but preferably approximately the middle (i.e. center line) in the up-down direction. In FIG. 4B, among 17 scan driving units (GDICs) 15 arranged in the up-down direction, eight scan driving units (GDICs) 15 on the upper side are the scan driving units (GDICs) 15 for the upper region, and nine scan driving units (GDICs) 15 on the lower side are the scan driving units (GDICs) 15 for the lower region.

As shown in FIG. 4C, the CPV signal line for CPV signal is connected from the controller 22 to (i.e. is common to) all the scan driving units (GDICs) 15.

In this embodiment, in order to let the lines L1 to Ln of the scan lines 5 of the radiation image capturing apparatus 1 sequentially go into the ON state so that signals of image data D are read, three types of signal, namely, the above-described STV signal (STV1, STV2), OE signal and CPV signal, are prepared.

In order to read image data D, the controller 22 first gives the STV signal (STV1) to the scan driving unit 15 for the $1^{st}$ line (L1) of the scan lines 5 of the radiation image capturing apparatus 1, and, at the time, also inputs the CPV signal so as to input a gate to the $1^{st}$ line (L1) (i.e. so as to make the $1^{st}$ line active), and if the controller 22 inputs the OE signal in this state, the TFTs 8 (i.e. switches) on the $1^{st}$ line (L1) become effective (ON state) so that, as to the $1^{st}$ line, the electric charges are released from the radiation detectors 7 to the signal lines 6 and read by the readout ICs 16 ("ROICs 16") as image data D.

In order to let the next line ($2^{nd}$ line (L2)) go into the ON state, the controller 22 inputs the CPV signal in the state in which the gate is on the $1^{st}$ line (L1) so as to shift the gate to the next line (i.e. the $2^{nd}$ line (L2)).

If, in the state in which the gate is on a line of the scan lines 5, the controller 22 inputs the CPV signal without inputting the OE signal (i.e. without letting the line go into the ON state), as to this line, electrical continuity of the radiation detectors 7 and the signal lines 6 remains broken, and hence without the image data D signal readout process with the readout ICs 16 and so forth performed on this line, the gate moves to the next line.

If 17 scan driving units (GDICs) 15 are arranged like this embodiment, but the STV signal line for STV1, the STV signal line for STV2, the OE signal line for OE signal and the CPV signal line for CPV signal are connected from the controller 22 to each of the scan driving units (GDICs) 15 individually, 68 signal lines are connected (i.e. drawn) from the controller 22. This requires the controller 22 to have a large number of I/O ports and accordingly requires use of a package having a large number of I/O ports. Further, this also makes drawing of the lines and so forth intricate and accordingly requires use of an expensive board having a large number of layers.

Meanwhile, in this embodiment, as described above, the STV signal line for STV1 is connected from the controller 22 to the top scan driving unit (GDIC) 15 only, the STV signal line for STV2 is connected from the top scan driving unit (GDIC) 15 to the second scan driving unit (GDIC) 15, the OE signal lines for OE signal are connected from the controller 22 to the scan driving units (GDICs) 15 for the upper region in such a way as to be common thereto and to the scan driving units (GDICs) 15 for the lower region in such a way as to be common thereto, and the CPV signal line for CPV signal is connected from the controller 22 to all the scan driving units (GDIC) 15 in such a way as to be common thereto. This can reduce the required number of I/O ports of the controller 22 and also simplify drawing of the lines and so forth.

<Control and Effects of Radiation Image Capturing Apparatus Specific to First Embodiment>

Control and effects of the radiation image capturing apparatus 1 specific to the first embodiment are described with reference to FIG. 5A and FIG. 5B.

Figure 5A:
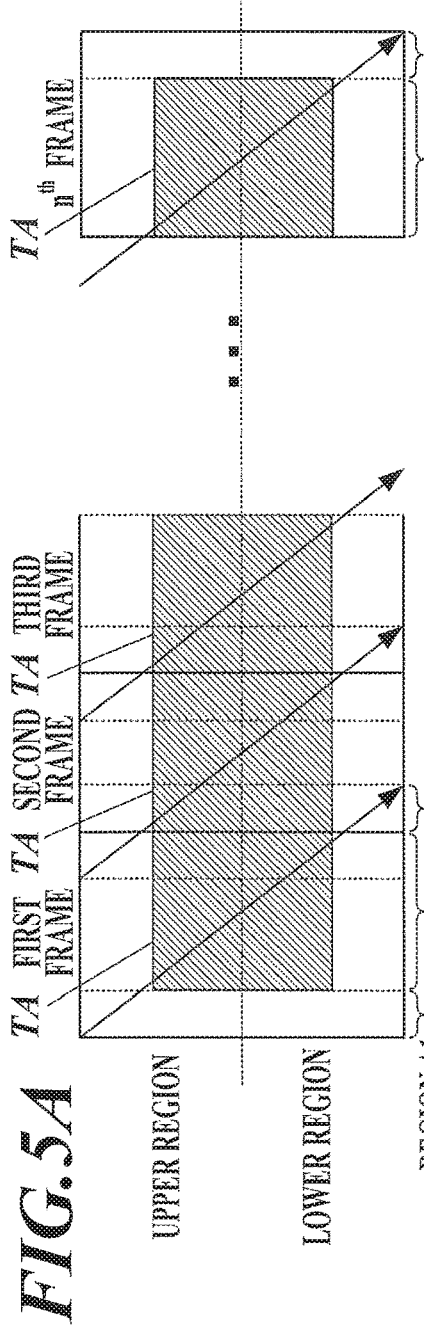
FIG. 5A is an illustration schematically showing trimming control in the first embodiment.

FIG. 5A is an illustration schematically showing trimming control on frames, and arrows in FIG. 5A indicate the direction in which the image data D signal readout process and gate shifting are performed. That is, the image data D signal readout process and gate shifting are performed from the upper left to the lower right in FIG. 5A sequentially. In FIG. 5A, a region A is a portion on the left side of a frame and does not contain the effective pixel region TA, a region B is a portion in a frame and contains the effective pixel region TA, and a region C is a portion on the right side of a frame and does not contain the effective pixel region TA. Regions A1, B1 and C1 represent the above-described regions of the first frame, and regions A2, B2 and C2 represent the above-described regions of the second frame, for example.

Figure 5B:
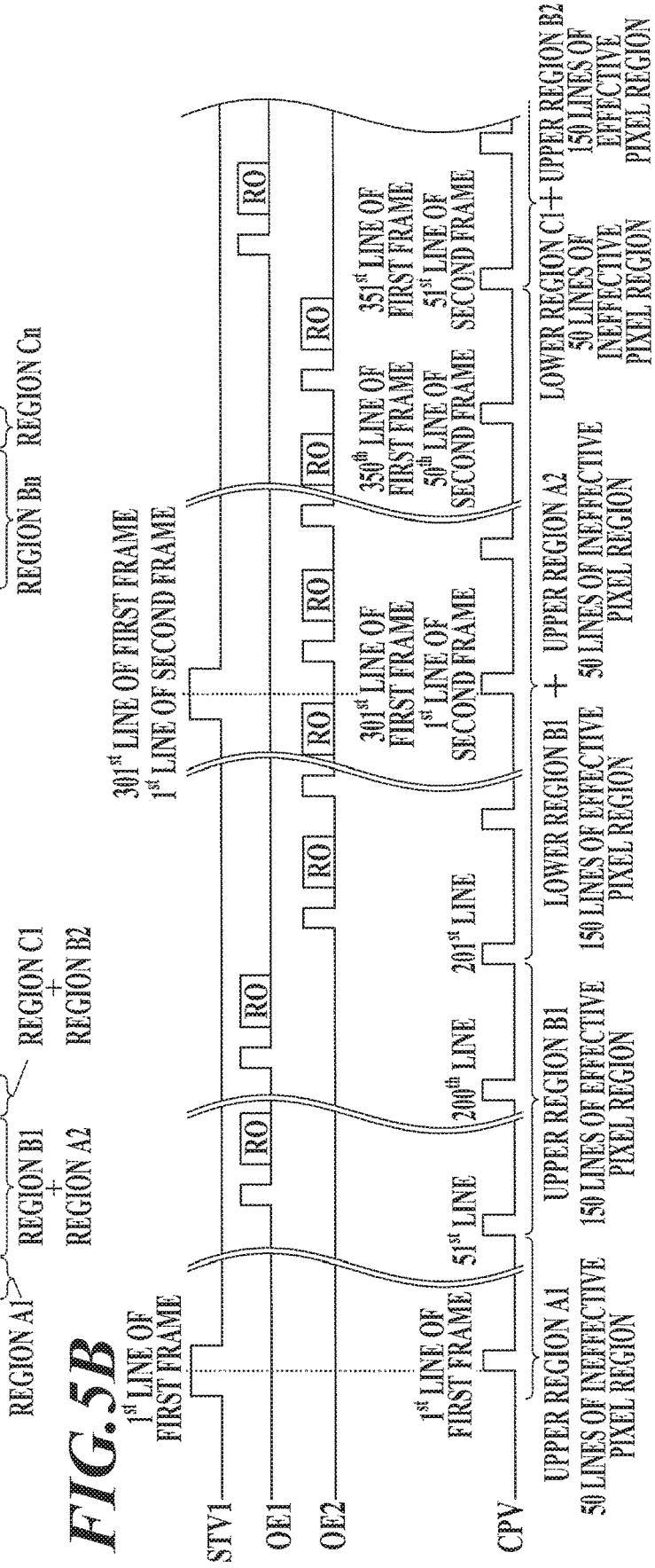
FIG. 5B is a timing chart showing input timings of STV signal, OE signal and CPV signal in the first embodiment.

FIG. 5B is a timing chart showing input timings at which signals are input in trimming control on one frame (as to STV1, to the $1^{st}$ line of/about the first frame and the $1^{st}$ line of/about the second frame) among the frames shown in FIG. 5A. In FIG. 5B, "RO" (ReadOut) represents that the readout ICs (ROICs) 16 read signals of image data D.

In this embodiment, first, the controller 22 of the radiation image capturing apparatus 1 detects the effective pixel region (region of interest) TA set by an operator (user), such as a radiologist, based on a command signal from an external apparatus, such as a console, an output value(s) of an X-ray sensor(s), or the like.

In this embodiment, as an example, the radiation detectors 7 are arranged in 400 (width)×400 (height) of the radiation image capturing apparatus 1 in a matrix. This area is taken as the imaging available region. Of this imaging available region, a region of 50 lines from the top and a region of 50 lines from the bottom are regions of ineffective pixels (hereinafter "ineffective pixel regions"). Hence, in this embodiment, as an example, 400 (width)×300 (height) that is approximately the center portion of each frame is the effective pixel region (region of interest) TA.

The imaging target site of a patient is placed at a position on the radiation image capturing apparatus 1, the position corresponding to the effective pixel region (region of interest) TA, and imaged. For the image data D signal readout process, the controller 22 first inputs STV1 to the scan driving unit (GDIC) 15 for the $1^{st}$ line about the first frame, and at the time, also inputs the CPV signal and accordingly inputs a pulse to the scan driving unit (GDIC) 15 for the $1^{st}$ line (L1).

The controller 22 further inputs only the CPV signal 50 times in this state so as to only shift the gate to the $51^{st}$ line, which is the top line of the effective pixel region TA.

Because 50 lines of the $1^{st}$ to $50^{th}$ lines are the ineffective pixel region of the upper region, the controller 22 does not input the OE signal and accordingly does not perform the image data D signal readout process with the readout ICs (ROICs) 16 and so forth.

When shifting the gate to the $51^{st}$ line, the controller 22 inputs only OE1 so that signals (i.e. electric charges/image data D) can be read from the upper region only. This lets the TFTs 8 on the $51^{st}$ line go into the ON state, so that, as to the $51^{st}$ line, the electric charges are released from the radiation detectors 7 to the signal lines 6 and read by the readout ICs (ROICs) 16 as image data D.

Thereafter, the controller 22 inputs the CPV signal and accordingly inputs a pulse to the scan driving unit (GDIC) 15 for the $52^{nd}$ line so as to shift the gate thereto.

For each of the $52^{nd}$ to $200^{th}$ lines too, the controller 22 inputs the OE signal (OE1), so that the TFTs 8 on the line become effective (ON state), and accordingly the signals (electric charges) are read by the readout ICs 16 (ROICs 16). This completes the image data D signal readout process on the effective pixel region TA of the upper region.

When shifting the gate to the $201^{st}$ line, the controller 22 inputs only OE2 so that signals (i.e. electric charges/image data D) can be read from the lower region only. This lets the TFTs 8 on the $201^{st}$ line go into the ON state, so that, as to the $201^{st}$ line, the electric charges are released from the radiation detectors 7 to the signal lines 6 and read by the readout ICs (ROICs) 16 as image data D.

Thereafter, the controller 22 inputs the CPV signal and accordingly inputs a pulse to the scan driving unit (GDIC) 15 for the $202^{nd}$ line so as to shift the gate thereto.

For each of the $202^{nd}$ to $350^{th}$ lines too, the controller 22 inputs the OE signal (OE2), so that the TFTs 8 on the line become effective (ON state), and accordingly the signals (electric charges) are read by the readout ICs 16 (ROICs 16). This completes the image data D signal readout process on the effective pixel region TA of the lower region.

In this embodiment, when, about the first frame, the $301^{st}$ line is reached, namely, when the remaining lines of the effective pixel region TA of the lower region become 50 lines, the controller 22 inputs STV1 to the scan driving unit (GDIC) 15 for the $1^{st}$ line about the second frame.

About the second frame, the controller 22 inputs only the CPV signal 50 times in this state so as to only shift the gate from the 1$^{st}$ line to the 50$^{th}$ line, namely, shift the gate to the front of the 51$^{st}$ line, which is the top line of the effective pixel region TA.

This makes it possible, while performing the image data D signal readout process on the effective pixel region TA of the lower region, to be specific, the 301$^{st}$ to 350$^{th}$ lines, about the first frame, to perform only gate shifting in the ineffective pixel region of the upper region about the second frame, thereby being able to do preparation (gate preparation) for the image data D signal readout process on the effective pixel region TA about the second frame.

Hence, it becomes possible to start the image data D signal readout process on the effective pixel region TA of the upper region about the second frame immediately after finishing the image data D signal readout process on the effective pixel region TA of the lower region about the first frame, and accordingly can eliminate waste of time in the processing time (i.e. time required for the image data D signal readout process). Further, although the state in which two gates are present at the same time occurs, no OE signal is input but only the CPV signal is input to the gate in the ineffective pixel region so as to only shift the gate. Hence, the image data D signal readout process on the effective pixel region TA is not affected by noise or the like and accordingly can be performed quickly with high accuracy.

Because 50 lines of the 351$^{st}$ to 400$^{th}$ lines are the ineffective pixel region of the lower region, the controller 22 inputs, about the first frame, only the CPV signal 50 times so as to only shift the gate from the 351$^{st}$ line to the 400$^{th}$ line.

When the gate in the first frame is on any of the 351$^{st}$ to 400$^{th}$ lines, the gate in the second frame is in the effective pixel region TA of the upper region. Hence, while only shifting the gate about the first frame, the controller 22 inputs OE1 about the second frame so that signals (i.e. electric charges/image data D) can be read from the upper region, to be specific, the 51$^{st}$ to 200$^{th}$ lines, only. This lets, about the second frame, the TFTs 8 on the 51$^{st}$ to 200$^{th}$ lines sequentially go into the ON state, so that, as to the 51$^{st}$ to 200$^{th}$ lines, the electric charges are released from the radiation detectors 7 to the signal lines 6 and read by the readout ICs (ROICs) 16 as image data D sequentially.

The above procedure is repeated for the effective pixel region TA of the lower region for the second frame and also repeated for the third and following frames, so that the image data D signal readout process is sequentially performed up to the n$^{th}$ frame.

As described above, according to this embodiment, the gate is sequentially shifted from the 1$^{st}$ line, i.e. the top line, to the n$^{th}$ line, i.e. the last line, whereas the image data D signal readout process is performed only on the effective pixel region TA. Hence, the image data D signal readout process is not performed on the unnecessary regions uselessly and accordingly can be performed efficiently and quickly.

Because the gate is sequentially shifted from the 1$^{st}$ line to the n$^{th}$ line, as the STV signal line for STV signal connected from/to the controller 22, the STV signal line for STV1 is enough. Further, the CPV signal line for CPV signal is common to all the scan driving units 15. Still further, as the OE signal line for OE signal, the OE signal line for OE1 to read signals from the effective pixel region TA of the upper region, namely, common to the scan driving units 15 for the upper region, and the OE signal line for OE2 to read signals from the effective pixel region TA of the lower region, namely, common to the scan driving units 15 for the lower region, are enough.

This can greatly reduce the number of signal lines to be connected from/to (i.e. drawn from) the controller 22 and can realize a quick trimming process with a reasonable package having a small number of I/O ports. This can also simplify wiring and reduce the number of layers of the board because the number of the drawn lines is small, and therefore can realize cost reduction.

Thus, according to the radiation image capturing apparatus 1 of this embodiment, the required number of I/O ports of the controller 22, which controls the scan driving units 15, can be reduced and accordingly cost reduction can be achieved, and also the time required for the image data D signal readout process can be reduced by appropriate trimming control.

Further, in this embodiment, the imaging available region of the radiation image capturing apparatus 1 is divided into the upper region and the lower region, and one OE signal line to input the OE signal is provided for each region.

Hence, for example, the image data D signal readout process on the effective pixel region TA of the lower region about a frame can be performed in parallel with gate shifting in the ineffective pixel region of the upper region about the next frame.

Thus, before the procedure for one frame is complete, STV1 is input for the next frame, which allows the image data D signal readout process to be performed continuously and unbreakably from the bottom of the effective pixel region TA of the lower region about one frame to the top of the effective pixel region TA of the upper region about the next frame, and accordingly makes the trimming process more efficient.

As described above, in this embodiment, the imaging available region of the radiation image capturing apparatus 1 is divided into two divisional regions, i.e. the upper region and the lower region, and one OE signal line to input the OE signal is provided for each region. However, the imaging available region of the radiation image capturing apparatus 1 is not limited to being divided into two divisional regions.

The imaging available region of the radiation image capturing apparatus 1 may be divided into more than two divisional regions, and one OE signal line to input the OE signal may be provided for each divisional region.

This can make the image data D signal readout process even more efficient.

Second Embodiment

Next, a second embodiment of the radiation image capturing apparatus of the present invention is described with reference to FIG. 6A to FIG. 7B. The second embodiment is different from the first embodiment in wiring of the OE signal line and the technique for trimming control only. Hence, hereinafter, the points different from the first embodiment are described in particular.

Figure 6A:
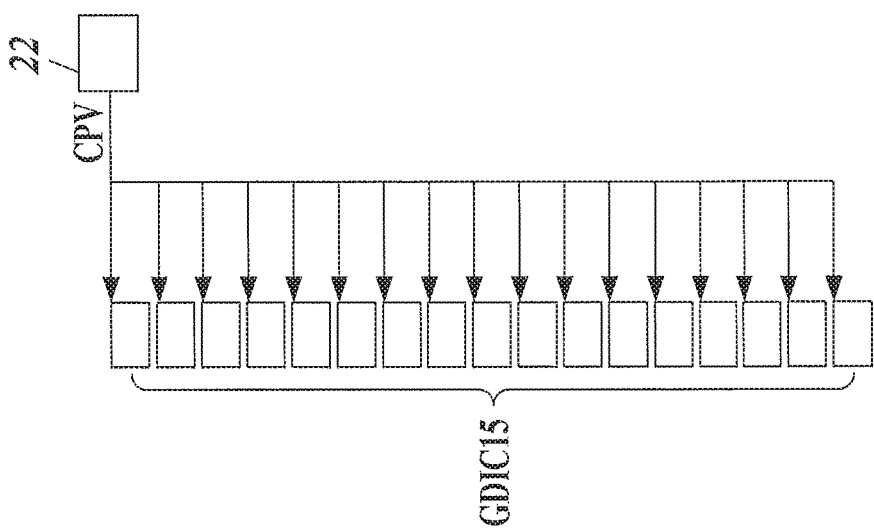
FIG. 6A shows an example of wiring of the STV signal lines in a second embodiment.
Figure 6B:
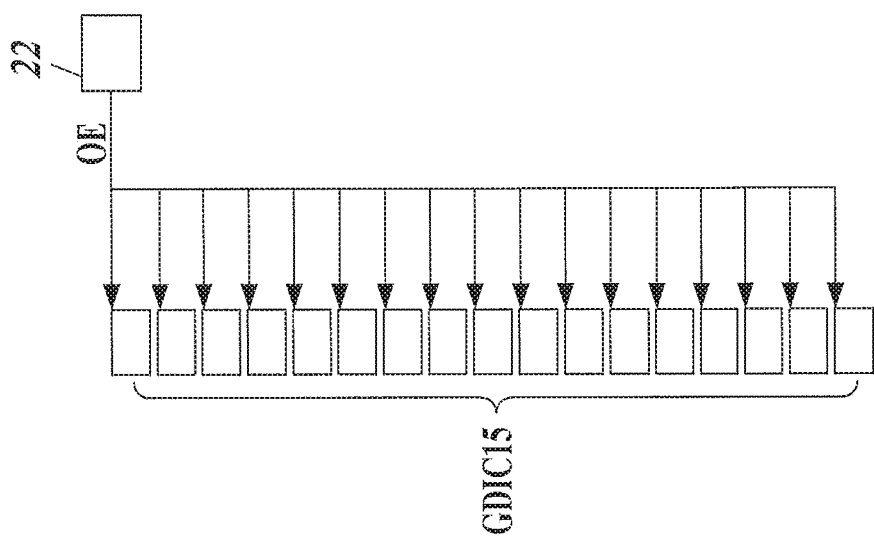
FIG. 6B shows an example of wiring of the OE signal line in the second embodiment.
Figure 6C:
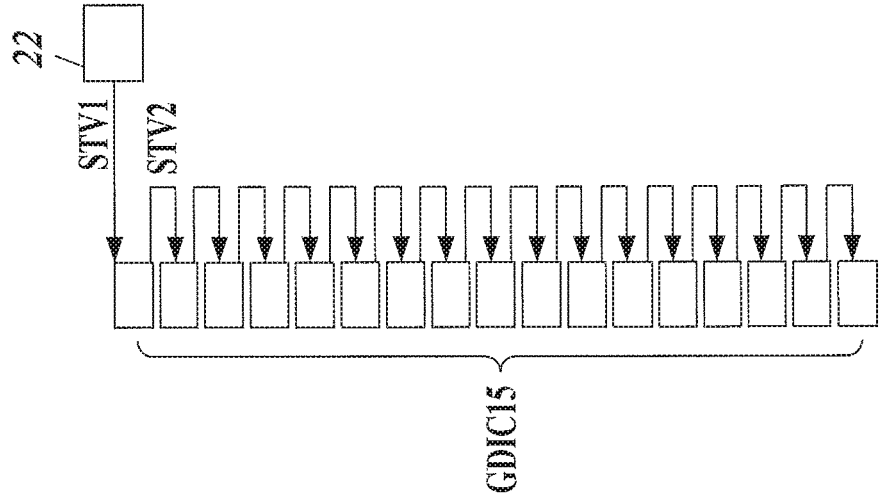
FIG. 6C shows an example of wiring of the CPV signal line in the second embodiment.

FIG. 6A shows an example of wiring of the STV signal line in this embodiment, FIG. 6B shows an example of wiring of the OE signal line in this embodiment, and FIG. 6C shows an example of wiring of the CPV signal line in this embodiment.

As shown in FIG. 6A and FIG. 6C, wiring of the STV signal line and wiring of the CPV signal line are the same as those in the first embodiment.

Meanwhile, wiring of the OE signal line is different from that in the first embodiment. As shown in FIG. 6B, the OE signal line is common to all the scan driving units (GDICs) 15, which is the same as the CPV signal line.

In this embodiment, unlike the first embodiment, the imaging available region is not divided, and one OE signal line is provided. This can further reduce the number of signal lines to be connected from/to the controller 22 and further simplify their wiring.

The configuration in the second embodiment is the same as that in the first embodiment except the above. Hence, the components same as those in the first embodiment are denoted by the reference numbers same as those in the first embodiment, and descriptions thereof are not repeated here.

Next, control and effects of the radiation image capturing apparatus 1 specific to the second embodiment are described with reference to FIG. 7A and FIG. 7B.

Figure 7A:
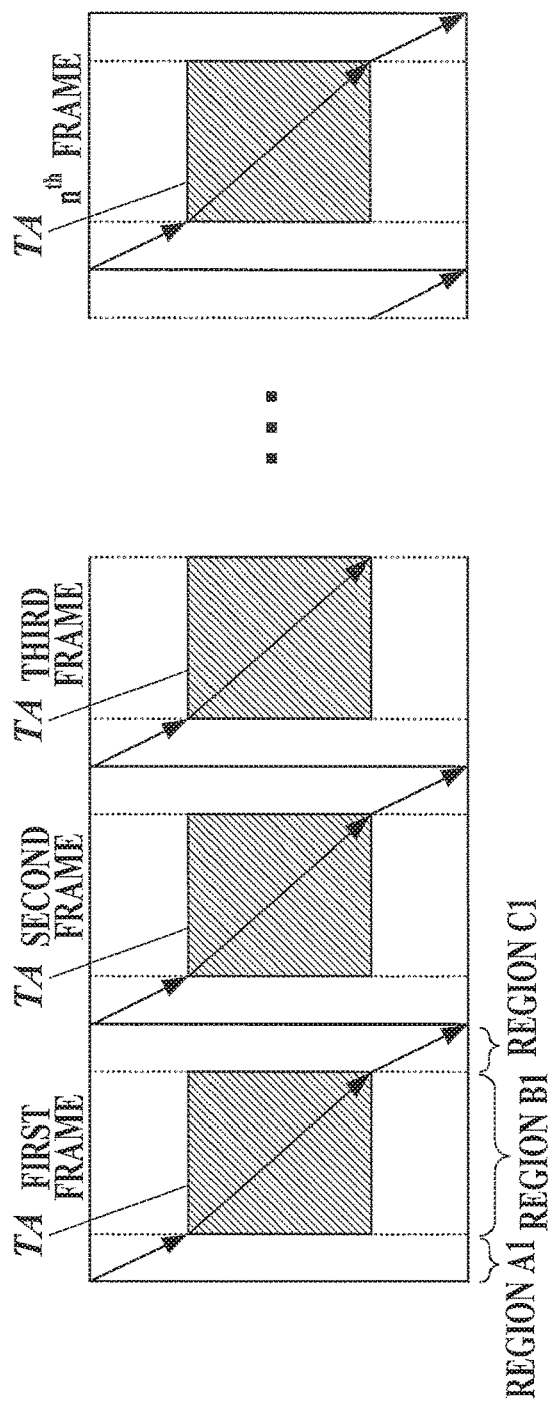
FIG. 7A is an illustration schematically showing trimming control in the second embodiment.
Figure 7B:
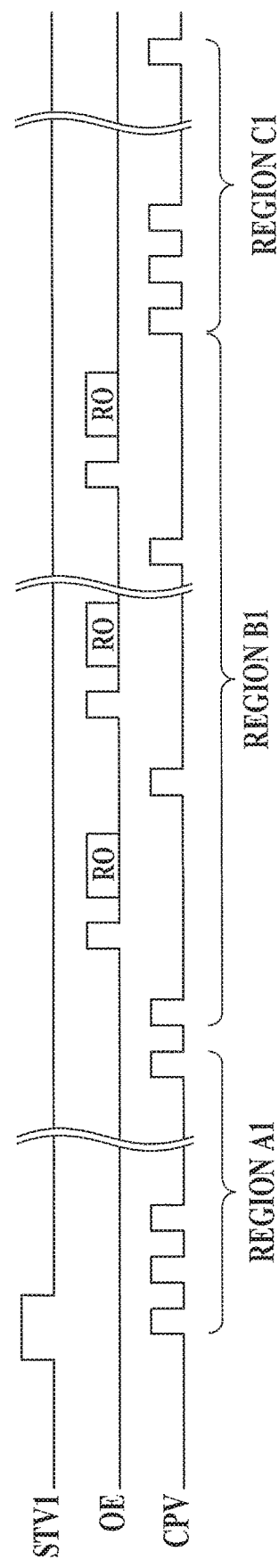
FIG. 7B is a timing chart showing input timings of the STV signal, the OE signal and the CPV signal in the second embodiment.

FIG. 7A is an illustration schematically showing trimming control in this embodiment, and FIG. 7B is a timing chart showing input timings of the STV signal, the OE signal and the CPV signal in this embodiment.

Arrows in FIG. 7A indicate the direction and speed in and at which the image data D signal readout process and gate shifting are performed. That is, the image data D signal readout process and gate shifting are performed from the upper left to the lower right in FIG. 7A sequentially. The gentle arrows, which have a large angle, indicate that at the portions indicated by these arrows, gate shifting is performed at low speed, whereas the sharp arrows, which have a small angle, indicate that at the portions indicated by these arrows, gate shifting is performed at high speed.

In this embodiment, first, as with the first embodiment, the controller 22 of the radiation image capturing apparatus 1 detects the effective pixel region (region of interest) TA set in the imaging available region.

The imaging available region and the effective pixel region (region of interest) TA in this embodiment are the same as those in the first embodiment.

The imaging target site of a patient is placed at a position on the radiation image capturing apparatus 1, the position corresponding to the effective pixel region (region of interest) TA, and imaged. For the image data D signal readout process, the controller 22 first inputs STV1 to the scan driving unit (GDIC) 15 for the $1^{st}$ line about the first frame, and at the time, also inputs the CPV signal and accordingly inputs a pulse to the scan driving unit (GDIC) 15 for the $1^{st}$ line (L1).

The controller 22 further inputs only the CPV signal 50 times in this state so as to only shift the gate from the $1^{st}$ line to the $50^{th}$ line, namely, shift the gate to the front of the $51^{st}$ line, which is the top line of the effective pixel region TA.

Because 50 lines of the $1^{st}$ to $50^{th}$ lines are the ineffective pixel region, the controller 22 does not input the OE signal and accordingly does not perform the image data D signal readout process with the readout ICs (ROICs) 16 and so forth.

As shown in FIG. 7A, to the scan driving units 15 for the $1^{st}$ to $50^{th}$ lines, which are the ineffective pixel region, the controller 22 inputs the CPV signal at higher speed than to the scan driving units 15 for the scan lines 5 of the effective pixel region TA.

This can shift the gate at high speed in the unnecessary region. Shifting the gate at high speed can be realized, for example, by shifting the gate at the maximum frequency of the scan driving unit(s) (GDIC(s)) 15, to be specific.

When shifting the gate to the $51^{st}$ line, the controller 22 inputs the OE signal so that signals (i.e. electric charges/ image data D) can be read. This lets the TFTs 8 on the $51^{st}$ line go into the ON state, so that, as to the $51^{st}$ line, the electric charges are released from the radiation detectors 7 to the signal lines 6 and read by the readout ICs (ROICs) 16 as image data D.

Thereafter, the controller 22 inputs the CPV signal and accordingly inputs a pulse to the scan driving unit (GDIC) 15 for the $52^{nd}$ line so as to shift the gate thereto.

For each of the $52^{nd}$ to $350^{th}$ lines too, the controller 22 inputs the OE signal, so that the TFTs 8 on the line become effective (ON state), and accordingly the signals (electric charges) are read by the readout ICs 16 (ROICs 16). When finishing the image data D signal readout process as to one line of the scan lines 5, the controller 22 inputs the CPV signal so as to shift the gate to the next line. Repeating the above completes the image data D signal readout process on the effective pixel region TA.

When shifting the gate to the $351^{st}$ line, to the scan driving units 15 for the $351^{st}$ to $400^{th}$ lines, which are the ineffective pixel region, the controller 22 again inputs the CPV signal 50 times at higher speed than to the scan driving units 15 for the scan lines 5 of the effective pixel region TA. This can shift the gate at high speed in the unnecessary region.

When the above procedure for the first frame finishes, the same procedure is repeated for the second and following frames, so that the image data D signal readout process is sequentially performed up to the $n^{th}$ frame.

The points other than the above are the same as those in the first embodiment, and hence descriptions thereof are not repeated here.

As described above, according to this embodiment, as with the first embodiment, the gate is sequentially shifted from the $1^{st}$ line, i.e. the top line, to the $n^{th}$ line, i.e. the last line, whereas the image data D signal readout process is performed only on the effective pixel region TA. Hence, the image data D signal readout process is not performed on the unnecessary regions uselessly and accordingly can be performed efficiently and quickly.

Because the gate is sequentially shifted from the $1^{st}$ line to the $n^{th}$ line, as the STV signal line for STV signal connected from/to the controller 22, the (one) STV signal line for STV1 is enough. Further, the OE signal line for OE signal and the CPV signal line for CPV signal are each common to all the scan driving units 15, and hence one OE signal line and one CPV signal line are enough.

This can reduce the number of signal lines to be connected from/to (i.e. drawn from) the controller 22 to the minimum and can realize a quick trimming process with a reasonable package having a small number of I/O ports. This can also simplify wiring and reduce the number of layers of the board because the number of the drawn lines is small, and therefore can realize cost reduction.

Further, in this embodiment, for the scan lines 5 other than the scan lines 5 of the effective pixel region TA, the controller 22 inputs the CPV signal at higher speed than for the scan lines 5 of the effective pixel region TA.

This can shift the gate at high speed in the unnecessary regions, and therefore the image data D signal readout process can be performed more efficiently and quickly.

In the above, some embodiments of the present invention are described. Needless to say, however, the present invention is not limited to the above embodiments, and can be modified in a variety of aspects without departing from the spirit of the present invention.

For example, in the second embodiment, frames are processed one by one. However, the technique for trimming control in the case where the OE signal line and the CPV signal line are each common to all the scan driving units 15 like the second embodiment is not limited to that described in the second embodiment.

For example, FIG. 8A is an illustration schematically showing trimming control in a modification of the second embodiment, and FIG. 7B is a timing chart showing input timings of the STV signal, the OE signal and the CPV signal in this modification of the second embodiment.

As shown in FIG. 8A and FIG. 8B, of the imaging available region, the regions that do not contain the effective pixel region TA are processed in parallel with one another. To be specific, for example, a region C1 of the first frame is processed in parallel with a region A2 of the second frame. This can make the trimming process less wasteful and more efficient.

More specifically, as with the first embodiment, the controller 22 first inputs STV1 to the scan driving unit (GDIC) 15 for the $1^{st}$ line about the first frame.

Then, about the first frame, the controller 22 inputs only the CPV signal 50 times in this state so as to only shift the gate from the $1^{st}$ line to the $50^{th}$ line, namely, shift the gate to the front of the $51^{st}$ line, which is the top line of the effective pixel region TA.

To the scan driving units 15 for the $1^{st}$ to $50^{th}$ lines, which are the ineffective pixel region, the controller 22 inputs the CPV signal at higher speed than to the scan driving units 15 for the scan lines 5 of the effective pixel region TA. This can shift the gate at high speed in the unnecessary region.

When shifting the gate to the $51^{st}$ line, the controller 22 inputs the OE signal so that signals (i.e. electric charges/image data D) can be read. This lets the TFTs 8 on the $51^{st}$ line go into the ON state, so that, as to the $51^{st}$ line, the electric charges are released from the radiation detectors 7 to the signal lines 6 and read by the readout ICs (ROICs) 16 as image data D.

Thereafter, the controller 22 inputs the CPV signal and accordingly inputs a pulse to the scan driving unit (GDIC) 15 for the $52^{nd}$ line so as to shift the gate thereto.

For each of the $52^{nd}$ to $350^{th}$ lines too, the controller 22 inputs the OE signal, so that the TFTs 8 on the line become effective (ON state), and accordingly the signals (electric charges) are read by the readout ICs 16 (ROICs 16). When finishing the image data D signal readout process as to one line of the scan lines 5, the controller 22 inputs the CPV signal so as to shift the gate to the next line. Repeating the above completes the image data D signal readout process on the effective pixel region TA.

When shifting the gate to the front of the $351^{st}$ line about the first frame, the controller 22 inputs STV1 to the scan driving unit (GDIC) 15 for the $1^{st}$ line about the second frame.

The controller 22 then inputs only the CPV signal 50 times. This can, while only shifting the gate from the $351^{st}$ line to the $400^{th}$ line about the first frame, only shift the gate from the $1^{st}$ line to the $50^{th}$ line about the second frame. That is, this can finish the procedure for the first frame, and can only shift the gate to the front of the $51^{st}$ line, which is the top line of the effective pixel region TA, about the second frame.

To the scan driving units 15 for the $351^{st}$ to $400^{th}$ lines, which is the ineffective pixel region, about the first frame, and to the scan driving units 15 for the $1^{st}$ to $50^{th}$ lines, which is the ineffective pixel region, about the second frame, the controller 22 inputs the CPV signal at higher speed than to the scan driving units 15 for the scan lines 5 of the effective pixel region TA, as with the second embodiment. This can shift the gate at high speed in the unnecessary regions.

The same procedure is repeated for the second and following frames, so that the image data D signal readout process is sequentially performed up to the $n^{th}$ frame.

Thus, in the modification, gate shifting in the ineffective pixel region in the second half of the first frame is performed in parallel with gate shifting in the ineffective pixel region in the first half of the second frame. Because they are performed simultaneously, the processing time can be reduced as compared with the second embodiment or the like in which frames are processed one by one, and therefore the image data D signal readout process can be performed more efficiently and quickly.

In the above embodiments, each frame is processed from the upper left to the lower right of the imaging available region, but not limited to being processed in this illustrated direction.

For example, in the case where the imaging available region is divided into the upper region and the lower region like the first embodiment, two STV signal lines to input the STV signal may be connected from the controller 22 to the scan driving unit 15 for the top scan line 5 and to the scan driving unit 15 for the last scan line 5, respectively.

In this case, the image data D signal readout process and gate shifting may be performed both from the upper left and from the lower left to the middle part (i.e. the center line) of the imaging available region in the up-down direction simultaneously.

In this case, the CPV signal lines to input the CPU signal may be connected from the controller 22 to the scan driving units 15 that belong to the upper region and to the scan driving units 15 that belong to the lower region, respectively.

This enables control, in either of the upper region and the lower region, to perform only gate shifting in the ineffective pixel region and to perform the image data D signal readout process on the effective pixel region TA by inputting the OE signal.

Further, the technique of inputting the CPV signal at high speed so as to shift the gate at high speed in the lines of the ineffective pixel regions described in the second embodiment may be appropriately combined with the technique described in the first embodiment.

This can further speed up the process (gate shifting) on the ineffective pixel regions.

Further, if the region that is used for imaging (i.e. the effective pixel region TA) when trimming control is performed is preset, individual STV signal lines and/or other signal lines may be connected from the controller 22 to the scan driving units 15 for the effective pixel region TA, and only the number of signal lines to be connected from the controller 22 to the scan driving units 15 for the other region(s) may be reduced.

For example, if the center portion of the imaging available region is preset as the effective pixel region TA, which is used in trimming control, for example, individual STV signal lines may be connected from the controller 22 to the scan driving units 15 for the effective pixel region TA, and one STV signal line (for STV1) may be connected from the controller 22 to any of the scan driving units 15 for the regions above and below the effective pixel region TA, or two STV signal lines (for STV1) may be connected from the controller 22 to any of the scan driving units 15 for the region above the effective pixel region TA and to any of the scan driving units 15 for the region below the effective pixel region TA, respectively.

In this case, the STV signal (STV1) can be input to any of the scan driving units 15 for the effective pixel region TA, which can realize trimming control having a high degree of freedom, and also reduce the number of signal lines to be connected from/to the controller 22 on the whole.

Further, the CPV signal line to input the CPV signal may not be common to all the scan driving units 15, and two or more CPV signal lines may be provided.

When the CPV signal line is common to all the scan driving units (GDICs) 15, the same CPV signal is input to all the scan driving units (GDICs) 15. Hence, it is impossible to input the CPV signal at high speed only to the scan driving units 15 (GDICs) for the ineffective pixel regions in the case where the ineffective pixel region and (a part of) the effective pixel region TA are processed at the same time like the first embodiment. However, when two or more CPV signal lines are provided, it is possible to shift the gate at high speed only in the ineffective pixel regions in the above case too.

Although embodiments of the present invention have been described and illustrated in detail, it is clearly understood that the same is by way of illustration and example only and not limitation, and the scope of the present invention should be interpreted by terms of the appended claims.

What is claimed is:

1. A radiation image capturing apparatus comprising:
    a plurality of scan lines of a $1^{st}$ line to an $n^{th}$ line;
    a plurality of signal lines;
    a plurality of radiation detectors two-dimensionally arranged in an imaging available region;
    a plurality of readout circuits that read electric charges released from the radiation detectors to the signal lines as image data;
    a plurality of switches that are arranged for the respective radiation detectors, and go into OFF state and break electrical continuity of the radiation detectors and the signal lines when OFF voltage is applied via the scan lines, and go into ON state and release the electric charges from the radiation detectors to the signal lines when ON voltage is applied via the scan lines;
    a plurality of scan driving units that switch voltage to be applied to the scan lines between the ON voltage and the OFF voltage;
    a controller that performs control to perform a readout process to read the image data from the radiation detectors;
    an output enable (OE) signal line to input, from the controller to the scan driving units, OE signal by which the ON voltage is applied to a predetermined scan line and the switches on the predetermined scan line go into the ON state; and
    a clock pulse vertical (CPV) signal line to input, from the controller to the scan driving units, CPV signal by which the predetermined scan line, to which the ON voltage is applied by the input of the OE signal, is shifted to a next scan line, wherein
    the controller detects an effective pixel region that is used in trimming control in which an area from which signals of the image data are read is limited, inputs the CPV signal to the scan driving units so as to sequentially shift the predetermined scan line from the $1^{st}$ line to the $n^{th}$ line, inputs the OE signal to the scan driving units so as to apply the ON voltage to a scan line of the detected effective pixel region, and does not input the OE signal to the scan driving units so as not to apply the ON voltage to a scan line outside the detected effective pixel region.

2. The radiation image capturing apparatus according to claim 1, wherein
    the imaging available region is divided into divisional regions to which the scan driving units belong, and
    the OE signal line is provided for each of the divisional regions.

3. The radiation image capturing apparatus according to claim 1, further comprising:
    a start vertical (STV) signal line to input an STV signal from the controller to the scan driving units, wherein
    the STV signal line is connected to the scan driving units in a daisy chain entirely or partly.

4. The radiation image capturing apparatus according to claim 1, wherein the CPV signal line is common to all the scan driving units.

5. The radiation image capturing apparatus according to claim 1, wherein the controller inputs the CPV signal to the scan driving units in such a way as to shift the predetermined scan line at higher speed in an ineffective pixel region outside of the effective pixel region than in the effective pixel region, wherein the ineffective pixel region is a region of the imaging available region not irradiated with radiation.

6. The radiation image capturing apparatus according to claim 1, wherein radiation images of multiple frames are continuously obtained in the radiation image capturing apparatus, and in reading the image data of the multiple frames, while reading the image data from the effective pixel region about a frame, the controller sequentially shifts the predetermined scan line in an ineffective pixel region about a next frame, wherein the ineffective pixel region is a region of the imaging available region not irradiated with radiation.

7. The radiation image capturing apparatus according to claim 1, wherein radiation images of multiple frames are continuously obtained in the radiation image capturing apparatus, and in reading the image data of the multiple frames, while sequentially shifting the predetermined scan line in an ineffective pixel region about a frame, the controller sequentially shifts the predetermined scan line in the ineffective pixel region about a next frame, wherein the ineffective pixel region is a region of the imaging available region not irradiated with radiation.

8. The radiation image capturing apparatus according to claim 7, wherein the controller inputs the CPV signal to the scan driving units in such a way as to shift the predetermined scan line at higher speed in the ineffective pixel region than in the effective pixel region.

9. The radiation image capturing apparatus according to claim 1, wherein
    radiation images of multiple frames are continuously obtained in the radiation image capturing apparatus,
    the imaging available region is divided into divisional regions to which the scan driving units belong,
    the OE signal line is provided for each of the divisional regions,
    the radiation image capturing apparatus further comprises a start vertical (STV) signal line to input an STV signal from the controller to the scan driving units, and
    the controller inputs the OE signal to the scan driving units from an OE signal line of the OE signal lines provided for the respective divisional regions so as to apply the ON voltage to the scan line of the effective pixel region about a frame, and without inputting the OE signal to the scan driving units from another OE signal line of the OE signal lines provided for the respective divisional regions so as not to apply the ON voltage to the scan line outside the effective pixel region about a next frame, inputs the STV signal to the scan driving units from the STV signal.

10. A radiation image capturing apparatus comprising:
a plurality of scan lines of a $1^{st}$ line to an $n^{th}$ line;
a plurality of signal lines;
a plurality of radiation detectors two-dimensionally arranged in an imaging available region;
a plurality of readout circuits that read electric charges released from the radiation detectors to the signal lines as image data;
a plurality of switches that are arranged for the respective radiation detectors, and go into OFF state and break electrical continuity of the radiation detectors and the signal lines when OFF voltage is applied via the scan lines, and go into ON state and release the electric charges from the radiation detectors to the signal lines when ON voltage is applied via the scan lines; a plurality of scan driving units that switch voltage to be applied to the scan lines between the ON voltage and the OFF voltage;
a controller that performs control to perform a readout process to read the image data from the radiation detectors;
an output enable (OE) signal line to input, from the controller to the scan driving units, OE signal by which the ON voltage is applied to a predetermined scan line and the switches on the predetermined scan line go into the ON state; and
a clock pulse vertical (CPV) signal line to input, from the controller to the scan driving units, CPV signal by which the predetermined scan line, to which the ON voltage is applied by the input of the OE signal, is shifted to a next scan line,
wherein the controller detects an effective pixel region that is used in trimming control in which an area from which signals of the image data are read is limited, inputs the CPV signal to the scan driving units so as to sequentially shift the predetermined scan line from the $1^{st}$ line to the $n^{th}$ line, inputs the OE signal to the scan driving units so as to apply the ON voltage only when the predetermined scan line is a scan line of the effective pixel region from which the image data is read, and inputs the CPV signal to the scan driving units in such a way as to shift the predetermined scan line at higher speed in an ineffective pixel region than in the effective pixel region.

* * * * *